(12) United States Patent
Ishida et al.

(10) Patent No.: US 8,263,145 B2
(45) Date of Patent: Sep. 11, 2012

(54) ENZYME PREPARATION AND PROCESS FOR PRODUCING FOOD USING THE SAME

(75) Inventors: Rikiya Ishida, Kawasaki (JP); Mika Uda, Kawasaki (JP); Yoshiyuki Kumazawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 2381 days.

(21) Appl. No.: 11/090,076

(22) Filed: Mar. 28, 2005

(65) Prior Publication Data

US 2005/0249839 A1 Nov. 10, 2005

Related U.S. Application Data

(63) Continuation of application No. PCT/JP03/12181, filed on Sep. 24, 2003.

(30) Foreign Application Priority Data

Sep. 26, 2002 (JP) ................................. 2002-281695

(51) Int. Cl.
*A23L 1/31* (2006.01)
(52) U.S. Cl. .......................................................... 426/56
(58) Field of Classification Search ...................... 425/56
See application file for complete search history.

(56) References Cited

U.S. PATENT DOCUMENTS

| 3,615,691 | A | * | 10/1971 | Van Den Oord et al. ..... 426/265 |
| 5,156,956 | A | * | 10/1992 | Motoki et al. ............... 435/68.1 |
| 5,162,506 | A | * | 11/1992 | Hadden ......................... 530/412 |
| 5,518,742 | A | | 5/1996 | Soeda et al. |
| 5,658,605 | A | | 8/1997 | Soeda et al. |
| 5,968,568 | A | | 10/1999 | Kuraishi et al. |
| 6,221,405 | B1 | * | 4/2001 | Sheehy et al. ................... 426/56 |
| 7,691,597 | B2 | | 4/2010 | Nakagoshi et al. |
| 2004/0131728 | A1 | | 7/2004 | Ootsuka et al. |
| 2005/0249839 | A1 | | 11/2005 | Ishida et al. |
| 2007/0202213 | A1 | | 8/2007 | Ishida et al. |

FOREIGN PATENT DOCUMENTS

| EP | 0 815 742 A2 | 1/1998 |
| JP | 7-227228 | 8/1995 |
| JP | 07-227228 | 8/1995 |
| JP | 10-070961 | 3/1998 |
| JP | 2001-149045 | 6/2001 |
| WO | WO 95/23524 | 9/1995 |

OTHER PUBLICATIONS

Fennema, O.R. ed. 1996. Food Chemistry. 3rd edition. Marcel Dekker, Inc. New York. p. 492. Third paragraph.*
U.S. Appl. No. 12/566,901, filed Sep. 25, 2009, Ishida, et al.
U.S. Appl. No. 08/563,587, filed Nov. 28, 1995, Sakai, et al.

* cited by examiner

*Primary Examiner* — D. Lawrence Tarazano
*Assistant Examiner* — Hamid R Badr
(74) *Attorney, Agent, or Firm* — Oblon, Spivak, McClelland, Maier & Neustadt, L.L.P.

(57) ABSTRACT

The present invention provides an enzyme preparation containing, as the active ingredient, an acidic or alkaline substance capable of shifting the pH value of the preparation toward a pH range wherein the expression of activity of a transglutaminase is inhibited when the transglutaminase is dissolved in the presence of collagen in a solution. The present invention also provides a process for producing a food by using the aforementioned enzyme preparation.

19 Claims, 1 Drawing Sheet

ENZYME PREPARATION AND PROCESS FOR PRODUCING FOOD USING THE SAME

CROSS-REFERENCE TO RELATED APPLICATIONS

The present application is a continuation of PCT/JP03/12181, filed on Sep. 24, 2003, which claims priority to Japanese Application No. JP 2002-281695, filed on Sep. 26, 2002, which are hereby incorporated by reference in their entireties.

BACKGROUND OF THE INVENTION

1. Field of the Invention

The present invention provides an enzyme preparation containing transglutaminase and a method for producing food products using the same. More specifically, the invention relates to an enzyme preparation containing 1) transglutaminase, 2) collagen and 3) an acidic or alkaline substance shifting the pH of the enzyme preparation when dissolved in a solution to a pH range where the expression of the transglutaminase activity is suppressed, and a process for producing food products using the enzyme preparation.

2. Discussion of the Background

Heretofore, there have been numerous reports of technique for applying effects of a crosslinking reaction in various proteins by transglutaminase in the fields of foods, medicinal products and chemical products. Among them, intensive research has been focused on a technique utilizing collagen (including gelatin, infra) and transglutaminase, in combination, thus engendering wide applicability in these technical fields.

For example, the following inventions have been reported: a method for producing modified collagen including a step of strengthening the inter-collagen molecular crosslinking with a transglutaminase (Japanese Patent No. 2897780); inventions of gelatin gel, gel-like foods and gelatin films with great thermal resistance and methods for producing the same (JP-A-6-98743, 7-227228 and Japanese Patent No. 2866746); and a method for producing restructured food with strong binding effects, using a combination of transglutaminase and collagen (JP-A-10-70961).

In addition to the field of food products, there have been reports about a collagen gel-type aromatic product with sufficient strength and thermal resistance, as well as a method for producing the same (JP-A-9-70428). As described above, the advantages obtained from the use of transglutaminase and collagen in combination has significant value in many fields of endeavor. Additionally, such a technique is advantageous.

Because collagen has extremely high reactivity with transglutaminase, however, the viscosity increases and gelation rate of solutions of transglutaminase and collagen in mixture are characteristically very rapid. Therefore, when producing gel-like food or restructured food various restrictions emerge during the production processes because the gelation of transglutaminase progresses immediately after transglutaminase is mixed with collagen.

When a solid food material is to be dispersed in a mixed solution of transglutaminase and collagen, for example, the dispersion procedure should be completed in a very short time frame until gelation starts. Accordingly, it is very difficult to produce a homogenous gel-like food at a mass scale.

As a method for producing restructured foods, a process is known where a paste-like material containing transglutaminase and collagen dissolved in water is added to a solid food material followed by mixing. When the gelation of the paste-like material is completed before the paste-like material is mixed in the solid food material, a food product with sufficient binding strength cannot be produced.

Further, collagen may sometimes be blended with curing agents and pickling liquids for use in the production of processed meat products such as ham, bacon and roasted pork. During the preparation of such pickling liquids, transglutaminase reaction with collagen progresses, disadvantageously, involving an increase in the viscosity to consequently prevent injection.

Therefore, to produce food products containing transglutaminase and collagen it is important that the transglutaminase reaction be tightly controlled during the production process. One method for suppressing the enzyme activity of transglutaminase is by dissolving transglutaminase in water at low temperature. This process utilizes the phenomenon that the transglutaminase activity is suppressed at low temperature. However, this process has an insufficient effect on the control of the physical properties. Additionally, such strict temperature control during the production process is not practical. Still further, gelation may be controlled by separately adding transglutaminase and collagen separately. However, such procedures are very laborious during the production process and not preferable.

In the production of restructured food alone, in addition to a process of adding a paste-like material of transglutaminase and collagen dissolved in water to a solid food material, a process of directly adding powdery or granular transglutaminase and collagen to a solid food material for binding has been previously described.

Enzyme preparations with a transglutaminase in blend in the related art are not preparations with wide applicability for use by any of the two processes above. Hence, an adhesive preparation with high applicability generating such highly satisfactory effects by any process, with no need to use a specific preparation for a specific production process, is strongly desired. Additionally, the enzyme preparation for binding comprising transglutaminase and collagen in blend as disclosed in JP-A-10-70961 can produce sufficient binding strength. At actual production sites, however, an enzyme preparation for binding generating stronger binding strength in a far shorter time period is needed.

SUMMARY OF THE INVENTION

It is an object of the present invention to provide a highly processable enzyme preparation containing transglutaminase and collagen in a blend, from which high-quality food products (gel-like food, restructured food, etc.) can be produced with minimal work by suppressing the gelation of the transglutaminase and collagen in mixture. The present invention also provides a method for producing food products such as gel-like food and restructured food using the enzyme preparation.

The present inventors have investigated new means to solve the problems outlined in the background of the present invention. Based on these investigations, the present inventors have discovered that by adjusting the pH of a solution, containing 1) transglutaminase and 2) collagen, to a range of pH 3 or more to less than or to a range of pH 10-12, the gelation of the solution can be suppressed. As such, the solution can maintain physical properties suitable for the production process of food products for a long period of time. Further, the inventors have found that the effect of transglutaminase cannot be manifested until a material with a pH buffer effect for example edible meat is added to and mixed with the solution containing 1) transglutaminase and 2) collagen as adjusted to the specific pH range, to neutralize the pH of the solution to an optimal reaction pH range for transglutaminase.

That is, the present invention relates to the embodiments described below:

1. An enzyme preparation comprising (1) transglutaminase, (2) collagen, and (3) an acidic or alkaline substance shifting the pH of the enzyme preparation, when dissolved in a solution, to a pH range wherein the expression of transglutaminase activity is suppressed. Within this embodiment, it is preferred that the pH range where the expression of transglutaminase activity is suppressed when the enzyme preparation is dissolved in the solution is pH 3 or more to less than pH 5 or pH 10-12. Further, within this embodiment, it is preferred that the acidic or alkaline substance is one or more selected from citric acid, malic acid, tartaric acid, sodium carbonate, potassium carbonate, trisodium phosphate, tripotassium phosphate, tetrasodium pyrophosphate, tetrapotassium pyrophosphate, glycine sodium salt, glycine potassium salt, sodium hydroxide, potassium hydroxide and calcium oxide (calcined calcium). Still further, within this embodiment the collagen is preferably derived from fish or shellfish.

2. An enzyme preparation comprising (1) transglutaminase, (2) collagen, and (3) an alkaline substance shifting the pH of the enzyme preparation, when dissolved in a solution, to a range of pH 9-12 and being directly mixed with a food material. In this embodiment, the alkaline substance is preferably one or more selected from sodium carbonate, potassium carbonate, trisodium phosphate, tripotassium phosphate, tetrasodium pyrophosphate, tetrapotassium pyrophosphate, glycine sodium salt, glycine potassium salt, sodium hydroxide, potassium hydroxide and calcium hydroxide and calcium oxide (calcined calcium). Also, within this embodiment, it is preferred that the collagen is derived from fish or shellfish.

3. A method for producing a food product, comprising dissolving the enzyme preparation according to embodiment 1 above in a solution, shifting the pH of the resulting solution to a pH range where the expression of transglutaminase activity is suppressed, and subsequently mixing the solution and a food material to shift the pH of the resulting mixture back to a pH range where the transglutaminase activity is expressed whereupon a transglutaminase reaction is carried out. In this embodiment, it is preferable that the pH range where the expression of transglutaminase is suppressed is pH 3 or more to less than pH 5 or pH 10-12. Still further, the pH range where the transglutaminase activity is expressed is pH 5-8. Even further, the food product is preferably a gel-like food or a restructured food.

4. A method for producing a food product, comprising directly mixing the enzyme preparation according to embodiment 1 or embodiment 2 above to food materials, without dissolving the enzyme preparation in a solution, to conduct the transglutaminase reaction. In this embodiment, it is preferred that the food product is a restructured product.

5. A method for producing a food product, comprising dissolving the enzyme preparation according to embodiment 1 above in a solution, shifting the pH of the resulting solution to a pH range where the expression of transglutaminase activity is suppressed, and subsequently injecting the resulting solution into a food material whereupon a transglutaminase reaction is carried out. In this embodiment, it is preferred that the pH range where the expression of transglutaminase activity is suppressed is pH 3 or more to less than pH 5 or pH 10-12. Further, within this embodiment, it is preferred that the food product is a whole muscle product produced without using minced meat.

6. A method for producing a food product, comprising dissolving in a solution three components of (1) transglutaminase, (2) collagen, and (3) an acidic or alkaline substance shifting the pH of the resulting solution to a pH range where the expression of transglutaminase activity is suppressed and mixing food materials with the resulting solution to shift the pH of the resulting mixture back to a pH range where the transglutaminase activity is expressed whereupon a transglutaminase reaction is carried out.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

DETAILED DESCRIPTION OF THE INVENTION

Figure 1:
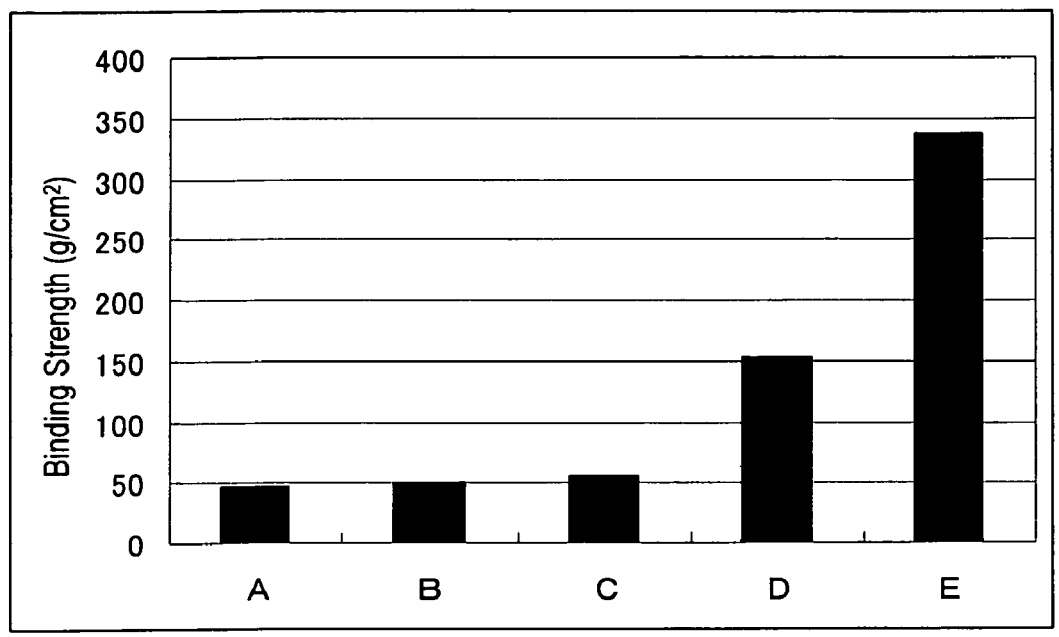
FIG. 1 shows the binding strength resulting from the use of various collagen types. A, B, C, D and E in this figure correspond to A, B, C, D and E in Table 1

Unless specifically defined, all technical and scientific terms used herein have the same meaning as commonly understood by a skilled artisan in enzymology, biochemistry, cellular biology, molecular biology, foods, medicinal products, chemical products and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

As used herein, the term "collagen" includes collagen and gelatin. Because it is very hard to discriminate collagen and gelatin from each other, currently, the term collagen as used in the art to which the present invention pertains commonly includes gelatin. Therefore, the term collagen is defined as described above.

Transglutaminase is an enzyme that catalyzes the acyl transfer reaction between the γ-carboxamide group of the glutamine residue in a protein or a peptide chain and primary amine, to form—for example—a crosslinked bond ε-(γ-Glu)-Lys in case that the primary amine is the lysine residue of a protein.

The transglutaminase that may be used in the present invention is a transglutaminase derived from any origin with no specific limitation as long as the transglutaminase has transglutaminase activity and includes transglutaminase derived from microorganisms (abbreviated as MTGase) of for example genus *Streptomyces* (for example, *Streptomyces mobaraensis* IFO 13819; *Streptoverticillium* is now classified into the genus *Streptomyces* by the current classification, which was classified in the genus *Streptoverticillium*) (JP-A-64-27471 and U.S. Pat. No. 5,156,956), transglutaminase derived from mammals such as guinea pig (JP-A-58-14964), transglutaminase derived from fishes such as cod (Nippon Suisan Gakkaishi (Japanese Journal of Fisheries Science), Nobuo Seki et al., Vol. 56, No. 1, page 125 (1990)), and transglutaminase existing in blood (also referred to as Factor XIII), and additionally includes genetically engineered transglutaminase (for example, JP-A-1-300889, JP-A-5-199883, JP-A-6-225775 and WO93/15234).

Therefore, the transglutaminase for use in accordance with the invention includes any transglutaminase described above. However, a transglutaminase derived from a microorganism is preferably used, because the transglutaminase can be commercially produced at a large scale and readily available at low cost.

Further, some transglutaminases requires calcium for the expression of activity (namely, calcium-dependent transglutaminase) and other transglutaminase never require calcium for expression of activity (namely, calcium-independent transglutaminase). Within the context of the present invention, either of these types may be used; however, from the perspective of ease of handling, it may be preferred to use a calcium-independent transglutaminase.

In accordance with the present invention, the activity of the transglutaminase is measured by the hydroxamate method (infra) and the unit thereof is also defined according to the hydroxamate method. Specifically, transglutaminase is added to a reaction solution containing substrates benzyloxycarbonyl-L-glutamylglycine and hydroxylamine in Tris-buffer at a temperature of 37° C. and pH 6.0, to generate hydroxamic acid, which is modified into an iron complex in the presence of trichloroacetic acid. Then, the absorbance of the reaction solution at 525 nm is measured to determine the hydroxamic acid generated by plotting on a standard curve. Subsequently, the amount of the enzyme generating 1μ mole of hydroxamic acid per one minute is defined as one unit (1 U) of the activity of transglutaminase (JP-A-64-27471 and U.S. Pat. No. 5,156,956).

In accordance with the present invention, any type of collagen may be used. Collagen from any material, with no specific limitation, may be used in accordance with the invention. Generally, the collagen is extracted from tissues such as bone, skin, cartilage, scale, and air bladder of animals and fishes and shellfishes. Particularly, it is known that collagen from fishes and shellfishes dissolves well in water. Thus, the collagen is very useful for applications requiring the preparation of collagen solution at low temperature.

For producing restructured foods, in particular, procedures at low temperature are indispensable from the standpoint of hygienic control and control of quality deterioration. Accordingly, collagen derived from fishes and shellfishes is appropriate for the production of restructured foods, because the collagen can dissolve at low temperature. It is indicated that such collagen generates stronger binding strength. Thus, preferably, collagen derived from fishes and shellfishes is used for the enzyme preparation of the present invention.

The amino acid composition of collagen is responsible for the solubility and melting point thereof. It is said that the solubility and melting point thereof depends on the content of proline and hydroxyproline. Therefore, the amino acid compositions of various collagen types (A to E) and the relation thereof with the effectiveness in binding are shown below in Table 1, as well as in FIG. 1.

TABLE 1

Amino Acid Compositions of Various Collagens
(Ratio of Amino Acid Residue in Number)

| | A | B | C | D | E |
|---|---|---|---|---|---|
| Hyp | 9.5 | 9.8 | 9.6 | 5.3 | 5.8 |
| Asp | 4.8 | 4.6 | 4.6 | 5.1 | 5.3 |
| Thr | 1.7 | 1.8 | 1.8 | 2.4 | 2.4 |
| Ser | 3.6 | 3.3 | 3.3 | 6.3 | 5.0 |
| Glu | 7.3 | 7.2 | 7.3 | 7.2 | 7.5 |
| Pro | 12.2 | 11.9 | 12.6 | 10.4 | 11.1 |
| Gly | 34.2 | 33.5 | 33.8 | 36.0 | 36.0 |
| Ala | 10.4 | 11.1 | 11.3 | 11.1 | 10.9 |
| Cys | 0.0 | 0.0 | 0.0 | 0.2 | 0.3 |
| Val | 2.2 | 2.3 | 2.3 | 1.9 | 1.7 |
| Met | 0.5 | 0.4 | 0.4 | 0.9 | 1.0 |
| Ile | 1.1 | 1.2 | 1.1 | 1.1 | 1.1 |
| Leu | 2.5 | 2.7 | 2.5 | 2.1 | 1.9 |
| Tyr | 0.3 | 0.3 | 0.0 | 0.0 | 0.0 |
| Phe | 1.4 | 1.5 | 1.6 | 1.5 | 1.4 |
| Lys | 2.9 | 2.8 | 2.7 | 2.7 | 2.5 |
| His | 0.6 | 0.5 | 0.4 | 0.9 | 1.0 |
| Arg | 4.8 | 5.1 | 4.8 | 5.2 | 5.2 |
| Total | 100.0 | 100.0 | 100.0 | 100.0 | 100.0 |
| Hyp + Pro(%) | 21.7 | 21.7 | 22.2 | 15.7 | 16.9 |

Consequently, it was discovered that the binding strength resulting from collagen with a total number of proline and hydroxyproline residues at 0.1% or more to less than 20% of the total number of amino acid residues was sufficiently large that such collagen was suitable for use in restructured food (PCT/JP02/02840). The collagen with such amino acid composition is typically derived from fishes and shellfishes.

In accordance with the present invention, the term collagen means collagen extracted and purified from tissues of animals and fishes and shellfishes. The extraction and decomposition method or the modification degree of the resulting collagen is not specifically limited. During the process of extraction, collagen is hydrolyzed to various extents, so the molecular weight distribution of the resulting collagen is frequently very wide. In accordance with the present invention, the term collagen includes so-called gelatin in a narrow sense, which is a modified form of collagen.

Further, the collagen is not necessarily a purified product. As such, the collagen may partially contain fats, carbohydrates, peptides, amino acids and the like, unless these inhibit the intended advantage of the present invention. Further, the collagen in accordance with the present invention includes not only collagen from a single origin but also collagen (including gelatin) from plural origins in mixture at an appropriate ratio.

Most characteristically, the enzyme preparation of the present invention contains: (1) transglutaminase, (2) collagen, and (3) an acidic or alkaline substance that shifts the pH of the enzyme preparation when dissolved in a solution to a pH range where the expression of the transglutaminase activity is suppressed.

In accordance with the present invention, the enzyme preparation is dissolved in a solution (e.g., an aqueous solution, fluid materials, etc.). Within this context, the acidic or alkaline substance contained in the enzyme preparation adjusts the pH of the solution to a pH range where the expression of transglutaminase activity is suppressed. Specifically, the pH is adjusted to a range of pH 3 or more to less than 5 or a range of pH 10 or more to pH 12 or less (i.e., pH 10-12).

Because transglutaminases hardly expresses its activity in the pH range described above, the gelation of the solution is suppressed. Therefore, the processability at the process of producing food products such as gel-like foods and restructured foods can be distinctly improved.

As the acidic or alkaline substance, any acidic or alkaline substance that is capable of adjusting the pH of the enzyme preparation when dissolved in a solution to a range of pH 3 to less than pH 5 or a range of pH 10-12 may be used. Generally, enzyme preparations are dissolved in water for use at about 10 to 25% solution. Hence, an acidic or alkaline substance capable of adjusting an aqueous 10 to 25% solution of the enzyme preparation to a range of pH 3 or more to less than pH 5 or a range of pH 10-12 may satisfactorily be selected. Additionally, two or more of such alkaline or acidic substance may be used in combination.

The alkaline substance (shifting the pH to an alkaline region) includes sodium, potassium, calcium or magnesium salt of inorganic acids, such as phosphoric acid and carbonic acid. Specifically, the alkaline substance includes sodium carbonate, potassium carbonate, trisodium phosphate, sodium polyphosphate, tetrasodium pyrophosphate, tripotassium phosphate, tetrasodium pyrophosphate, tetrapotassium pyrophosphate, glycine sodium salt, glycine potassium salt, sodium hydroxide, potassium hydroxide, and calcium oxide (also referred to as calcined calcium).

Additionally, the acidic substance (shifting the pH to an acidic region) includes citric acid, adipic acid, gluconic acid, acetic acid, lactic acid, fumaric acid, malic acid, tartaric acid and sulfuric acid.

However, these examples of alkaline and acidic substances are not intended to be limiting. As long as the object of the invention can be attained, any pH-adjusting substances are satisfactory. Among them, particularly preferable acidic or alkaline substances include citric acid, malic acid, tartaric acid, sodium carbonate, potassium carbonate, trisodium phosphate, tripotassium phosphate, tetrasodium pyrophosphate, tetrapotassium pyrophosphate, glycine sodium salt, glycine potassium salt, sodium hydroxide, potassium hydroxide, and calcium oxide (also referred to as calcined calcium).

The amounts of the essential elements for the enzyme preparation of the invention, namely (1) transglutaminase, (2) collagen, and (3) such acidic or alkaline substance to be blended therein are not specifically limited. However, preferable ranges include, per 1 g of the enzyme preparation, (1) transglutaminase—1 U to 200 U, particularly preferably 10 U to 150 U; and (2) collagen—0.1 g to 0.9 g, particularly preferably 0.2 g to 0.6 g. Additionally when an acidic or alkaline substance is blended at an amount to adjust the initial pH of the enzyme preparation to a range where the expression of transglutaminase activity is suppressed, namely a range of pH 3 or more to less than pH 5 or a range of pH 10-12, no particular limitation exists.

For the enzyme preparation of the present invention, additionally, the elements (1) transglutaminase, (2) collagen and (3) such acidic or alkaline substance are not necessarily blended in one container but may be placed in a set of separate containers, which is in the form of so-called "kit". In accordance with the present invention, various appropriate ingredients may be blended, other than the elements (1) transglutaminase, (2) collagen and (3) the acidic or alkaline substance shifting the pH of the enzyme preparation when dissolved in a solution to a pH range where the expression of the transglutaminase activity is suppressed.

The enzyme preparation of the present invention may contain, for example, the following additional bulking agents known for use in food products: saccharides such as lactose, sucrose, maltose, maltitol, sorbitol and trehalose, dextrin, branched dextrin, cyclodextrin, thickeners such as starches, polysaccharides, gums, pectin, agar, carrageenan, and alginic acid; and the like.

Additionally, the enzyme preparation may contain caseins, various animal proteins, and vegetable proteins such as soybean protein and wheat protein.

Still additionally, the enzyme preparation may be blended appropriately with seasonings, purified sugar, spices, colorants, color developing agents, organic acids such as ascorbic acid and salts thereof, emulsifiers, oils and fats, microparticle silicone dioxide and the like.

When used as a pickling liquid, the aforementioned ingredients may not necessarily be blended in the enzyme preparation but may be added to a pickling liquid separately from the enzyme preparation of the invention.

The method for producing food products such as gel-like food and restructured food using the enzyme preparation of the present invention is now described. The most significant feature of the invention is the control of the viscosity of a solution containing transglutaminase and collagen, by adjusting the pH of the solution to a range of pH 3 or more to less than pH 5 or a range of pH 10-12.

Figure 2:
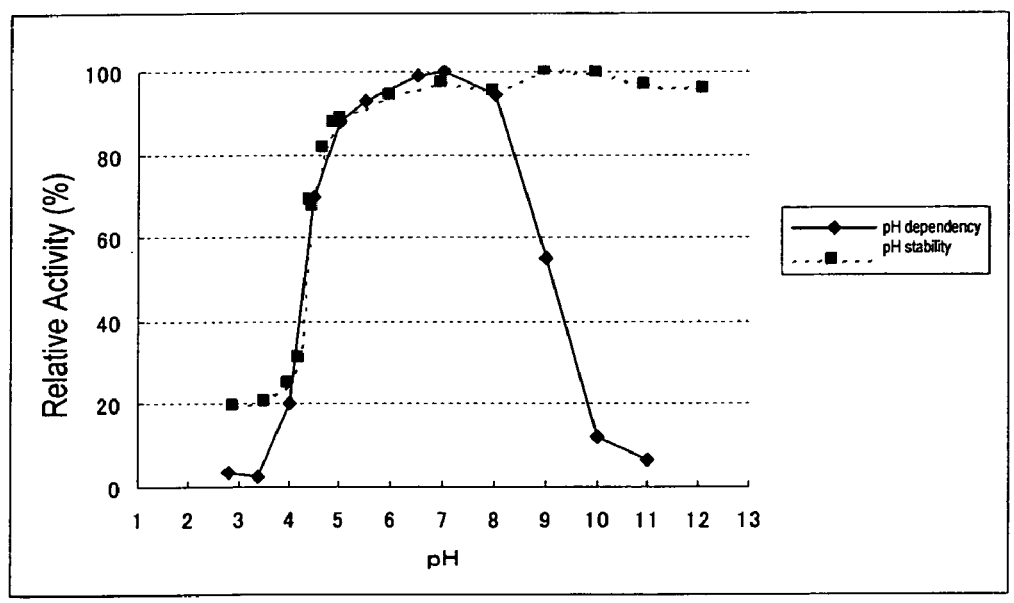
FIG. 2 shows the pH dependency and stability of transglutaminase activity.

This can be described on the basis of the pH dependence and stability of the transglutaminase activity. FIG. 2 shows a graph depicting the pH dependence of transglutaminase activity and that that the optimal pH of transglutaminase is pH 5 to pH 8. Further, FIG. 2 shows that the expression of the transglutaminase activity is significantly reduced outside the optimal pH range, apparently indicating extremely poor progress of transglutaminase reaction. However, the inventors also focused their attention to the finding shown in the graph of the pH stability in FIG. 2 that the stability of transglutaminase was retained fairly well in a range outside the optimal pH range, particularly in an alkaline region. In other words, when the pH of the solution is shifted to a pH range where the expression of transglutaminase activity is much suppressed and then shifted back to the optimum pH region of transglutaminase activity after conducting an operation such as dispersion to food material, a transglutaminase reaction takes place. In such manner, the problems of the related art can be overcome, so that satisfactory advantages can be yielded.

Any pH shifting method may be satisfactory, with no limitation, as long as the method enables the shifting to a pH range where the transglutaminase activity is obtainable. The pH shifting method includes for example a step of mixing the solution with a food material with a pH buffer effect. Edible meat such as beef, pork, foul meat, chicken meat and fish meat, as well as fluids generally called drip, such as fluids, blood, tissue fluids, etc. of animals have very large pH buffer effects.

By dissolving the enzyme preparation in a solution and mixing the solution while suppressing gelation with food materials, the pH can then be shifted to the optimal pH range (pH 5 or more to pH 8 or less) to progress the enzyme reaction. In such manner, desired food products, for example gel-like food and restructured food, can be produced.

As described above, the gelation of the solution can be suppressed in the pH range where the expression of the transglutaminase activity is suppressed. When pork meat and the like are added to and mixed with the solution, the pH buffer effect of pork meat and the like can adjust the resulting mixture to pH 5 to pH 8. By injecting a pickling liquid containing the enzyme preparation of the invention into food materials for ham, bacon and roasted pork, the same effect can be procured involving the recovery of whole muscle products produced without using minced meat (ham, bacon, roasted pork, etc.) of high quality.

When a food material has no such pH buffer effect, unlike cattle meat, the addition of an acidic or alkaline substance or a food material treated with acids or alkalis may neutralize the solution. By adding such food material to the solution, for example, a gel-like food dispersing therein fresh or dried materials can be produced in a reasonable manner. Only if the solution can be neutralized as described above, any food material can be added with no specific limitation to the size or shape of the food material or whether or not the food material is solid or liquid.

As the food material for use in accordance with the present invention, the following edible meats may be used: beef, pork, horsemeat, mutton, goat meat, poultry and chicken meat. In addition, various fishes, shellfishes, crustacean species such as shrimp and crab, molluscan species such as squid and octopus and fish eggs such as separated salmon roe and salmon roe in one fillet form can also be utilized. It is needless to say that food materials other than those described above can also be used or two or more of such food materials may satisfactorily be used in combination.

Because the effect on the suppression of the transglutaminase reaction and the effect on the acceleration of the reaction via pH adjustment depend on the temperature, the amount of transglutaminase, the type and amount of a substrate protein, the reaction time and the like, the resulting effect depends on each of the production conditions. Depending on what is the intended final product type, various conditions described above should be determined.

A food product for which the present invention is particularly effective is restructured food. In other words, binding meat pieces together produces the "restructured" food. The production of the restructured product is now described below in detail.

The production process of restructured food is divided in two groups. The first is a process (water dissolution method) of dissolving an enzyme preparation for adhesion in a solution (water or fluid materials or the like) and adding the resulting paste-like mixture to solid materials for molding and adhesion. The other is a process (powder sprinkling method) of directly adding an enzyme preparation for binding to solid food materials, with no dissolution of the enzyme preparation in any solution (water or fluid materials or the like).

First, the water dissolution method using the enzyme preparation of the invention is described. In the first step, expression of the transglutaminase activity is suppressed by dissolving in water or the like the enzyme preparation containing (1) transglutaminase, (2) collagen, and (3) an acidic or alkaline substance shifting the pH of the enzyme preparation when dissolved in a solution to a pH range where the resulting solution is adjusted to a range of pH 3 or more to less than pH 5 or a range of pH 10-pH 12. In the pH range, the expression of the transglutaminase activity is suppressed and no gelation commences.

Then, food materials (e.g., beef) are mixed with the solution (or fluid materials). Because such food materials have a pH buffer effect, the pH of the resulting mixture shifts to a pH range where transglutaminase activity is expressed (i.e., a range of pH 5-8) via the addition and mixing thereof. When the pH never reaches the range of pH 5-8 even after the addition and mixing of the food materials, a reagent for pH adjustment is added to shift the pH of the mixture to the optimal pH range for transglutaminase reaction, namely the range of pH 5-8.

Generally, the transglutaminase reaction may be conducted at 0 to 55° C. for 10 seconds to 24 hours. Naturally, these reaction conditions are not limiting. As described above, the transglutaminase reaction starts, so that a restructured food product can be obtained.

For such production, the enzyme preparation of the present invention is most appropriately used. However, (1) transglutaminase, (2) collagen, and (3) an acidic or alkaline substance shifting the pH of the enzyme preparation to a pH range where the expression of the transglutaminase activity is suppressed may satisfactorily be purchased and used, separately. In this case, transglutaminase, collagen and the acidic or alkaline substance may be mixed together as they remain powdery; and then, the resulting mixture is dissolved in a solution (e.g., water). Otherwise, the individual substances may be first dissolved in water and the like and then, the resulting solutions are mixed together. By dissolving collagen in water and the like, additionally, an acidic or alkaline substance may be used to adjust the pH of the resulting solution, to which transglutaminase is then added.

Most importantly, the pH of the solution should be shifted to the pH range (a range of pH 3 or more to less than pH 5 or a range of pH 10-12) where the transglutaminase activity is suppressed.

The following procedures are identical to those when using the enzyme preparation.

Specifically, the solution and food materials are mixed together, to adjust the resulting mixture to the pH range where transglutaminase activity is expressed, namely the range of pH 5-8, to progress transglutaminase reaction to obtain restructured food.

The powder sprinkling method of using the enzyme preparation of the present invention is now described below. The powder sprinkling methods have a point different from water solution methods in that the enzyme preparation with no dissolution is directly sprinkled on food materials to which the enzyme preparation itself is intended to adhere. When the enzyme preparation is directly added to food materials as described above, the pH of the surfaces adhering together is shifted to the pH range suitable for transglutaminase reaction via their pH buffer effects. Thus, a stronger gel is formed, to attain stronger binding strength.

In one embodiment, the enzyme preparation may contain: (1) transglutaminase, (2) collagen, and (3) an alkaline substance shifting the enzyme preparation when dissolved in a solution to a range of pH 9-12, in addition to the enzyme preparation for use in the water solution methods. However, the enzyme preparation can be used only for the powder sprinkling methods including a step of directly adding the enzyme preparation to food materials. The alkaline substance includes for example sodium carbonate, potassium carbonate, trisodium phosphate, tripotassium phosphate, tetrasodium pyrophosphate, tetrapotassium pyrophosphate, glycine sodium salt, glycine potassium salt, sodium hydroxide, potassium hydroxide and calcium oxide (calcined calcium).

After these enzyme preparations are mixed into raw food materials, transglutaminase reaction should commence. Herein, the conditions for the transglutaminase reaction are not limited but generally include 0° C. to 55° C. for 10 seconds to 24 hours. In such manner, restructured food can be obtained.

In accordance with the invention, further, the enzyme preparation containing (1) transglutaminase, (2) collagen, and (3) an acidic or alkaline substance shifting the pH of the enzyme preparation when dissolved in a solution to a pH range where the expression of the transglutaminase activity is suppressed can be used for both the water dissolution methods and the powder sprinkling methods. Thus, the enzyme preparation has such wide applicability. Additionally, the enzyme preparation generates very strong binding strength.

The enzyme preparation is preferably used in a simple manner for producing restructured food by the powder sprinkling methods. However, (1) transglutaminase, (2) collagen, and (3) an acidic or alkaline substance shifting the pH of the enzyme preparation when dissolved in a solution to a pH range where the expression of the transglutaminase activity is suppressed may satisfactorily be purchased separately, to produce restructured foods by the powder sprinkling methods.

Alternatively, (1) transglutaminase, (2) collagen, and (3) an alkaline substance shifting the pH of the enzyme preparation when dissolved in a solution to a pH range of pH 9-12 may satisfactorily be purchased separately as well, to produce restructured food by the powder sprinkling method.

In accordance with the present invention, the enzyme preparation containing (1) transglutaminase, (2) collagen, and (3) an acidic or alkaline substance shifting the pH of the enzyme preparation when dissolved in a solution to a pH range where the expression of the transglutaminase activity is suppressed is used for producing restructured food as described above. Additionally, the enzyme preparation can be used for producing gel-like food other than restructured food. The gel-like food includes for example jellies (jellies including highly thermally stable jellies and jellies containing material pieces such as vegetable pieces and fruit pieces); sweet jelly of beans; gummy candies; and food products like shark fin. Additionally, the enzyme preparation can be used for producing pickling liquids and whole muscle products without using minced meat (ham, bacon, roasted pork, etc.) prepared by using pickling liquids.

For production of any of the restructured food, gel-like food, and whole muscle products without using minced meat prepared by using pickling liquids, transglutaminase is generally used at an amount of 0.001 U to 100 U, preferably 0.01 U to 10 U and collagen is used at an amount of 0.0001 g to 0.9 g, preferably 0.001 g to 0.5 g, per 1 g of a final product in accordance with the invention. Even in the case of using transglutaminase and collagen in combination in the form of an enzyme preparation or separately, transglutaminase and collagen are satisfactorily used in the amount ranges.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1

Measuring Gelation Time when Using Fish Collagen

Commercially available transglutaminase ("Activa" TG at a specific activity of 1,000 U/g product, manufactured by Ajinomoto Co., Inc.) derived from the genus *Streptomyces* (*Streptomyces mobaraensis* IFO 13819) was used as the transglutaminase. Additionally, fish collagen "HMW Fish Gelatin" (under trade name) manufactured by Kenny & Ross Ltd. was used as the fish collagen. "APH-250" (under trade name) manufactured by Nitta Gelatin Co. was used as the animal collagen.

Water (24 g) was added to 3.2 g of the fish collagen "HMW Fish Gelatin" (manufactured by Kenny & Ross Ltd.; under trade name; the trade name includes the term Gelatin but herein, the product is referred to as fish collagen), to dissolve the collagen at ambient temperature. The pH of the resulting solution was adjusted to the individual pHs shown in Table 2 below with aqueous 27% sodium hydroxide solution or conc. hydrochloric acid. To the resulting pH-adjusted solutions transglutaminase (0.48 g) dissolved in 8 g of water was added with agitation for 10-sec and the pH of the mixtures was measured. By employing a rheometer manufactured by Haake GmbH & Co., the storage modulus and the loss modulus of the aforementioned mixtures were measured at intervals following transglutaminase addition to determine the gelation time at which the storage modulus coincided with the loss modulus. As a control, transglutaminase was added to an aqueous solution of the fish collagen (HMW Fish Gelatin) and the pH was not adjusted. The gelation time of the control mixture was measured in the same manner as described above. The results are shown in Table 2.

TABLE 2 pH dependence of gelation time of fish collagen and transglutaminase

| pH of mixtures of fish collagen and transglutaminase | Gelation time (in minute) |
| --- | --- |
| 2.5 | >60 |
| 3 | >60 |
| 4 | 30 |
| 6 | <1 |
| 7 | <1 |
| 8 | 1 |
| 9 | 3 |
| 9.5 | 4 |
| 10 | 10 |
| 11 | >60 |
| 12 | >60 |
| Control (pH 5) | 3 |

As shown in Table 2, the aqueous solution of the fish collagen could delay the gelation via the transglutaminase reaction, when the aqueous solution of the fish collagen was adjusted to a range of less than pH 5 or a range of pH 10 or more.

EXAMPLE 2

Measuring Gelation Time in Using Animal Collagen

Water (24 g) was added to 3.2 g of animal collagen ("APH-250" manufactured by Nitta Gelatin Co.), and the collagen was dissolved in a 40° C. water bath. The pH of the resulting solution was adjusted to the individual pHs shown in Table 3 with aqueous 27% sodium hydroxide solution or conc. hydrochloric acid. To the resulting pH-adjusted solutions 0.48 g of the transglutaminase, which was used in Example 1, was added ("Activa" TG at a specific activity of 1,000 U/g product, manufactured by Ajinomoto Co., INC.) after dissolution in 8 g of water with 10-sec agitation and the pH of the mixtures was measured. Subsequently, the storage modulus and the loss modulus were measured at 40° C. at intervals after transglutaminase addition to determine the gelation time when the storage modulus coincided with the loss modulus using a rheometer manufactured by Haake GmbH & Co. As a control, transglutaminase was added to an aqueous solution of the animal collagen (APH-250) and the pH was not adjusted. The gelation time of the control mixture was measured in the same manner as described above. The results are shown in Table 3.

TABLE 3 pH dependence of gelation time with animal collagen and transglutaminase

| pH of mixtures of animal collagen and transglutaminase | Gelation time (in minute) |
|---|---|
| 2.5 | >60 |
| 3 | >60 |
| 4 | 6 |
| 6 | 1 |
| 7 | 1 |
| 8 | 2 |
| 9 | 2.5 |
| 10 | 5 |
| 11 | 37 |
| 12 | >60 |
| Control (pH 5) | 3.5 |

As shown in Table 3, the aqueous solution of the animal collagen could delay the gelation via transglutaminase reaction, like the aqueous solution of the fish collagen, when the aqueous solution of the animal collagen was adjusted to a range of less than pH 5 or a range of pH 10 or more. At pH 4 and pH 10, however, the fish collagen could delay the gelation time longer.

EXAMPLE 3

Production of Restructured Pork with Transglutaminase and Fish Collagen (by Water Solution Method)

6 g of the fish collagen used in Example 1 was dissolved in 50 g of water, and the pH was adjusted with aqueous 27% sodium hydroxide solution or conc. hydrochloric acid to the individual pHs shown below in Table 4. 0.9 g of the same transglutaminase ("Activa" TG at a specific activity of 1,000 U/g product, manufactured by Ajinomoto Co., Inc.) as used in Example 1 dissolved in 10 g of water was added to the collagen solutions with 10-second agitation and the pH of the mixtures was measured. Following pH measurement, the resulting solutions were maintained for 10 minutes to confirm the presence or absence of gelation.

When the mixture solution was not gelled even after 10 minutes, a total of 300 g of pork thigh pieces (about 2-cm cube) was added to and mixed sufficiently with 13.4 g of the mixture solution to permit the mixture of collagen and transglutaminase to thoroughly mix with the meat pieces. The amount of transglutaminase then used was 0.6 U per one gram of the final product, while the fish collagen was used at an amount of 0.004 g per one gram of the final product.

A casing tube with a folding width of 75 mm was filled with the resulting mixture and the casing tube was maintained at 5° C. for 2 hours to permit the effectuation of the transglutaminase reaction. After the reaction, the casing tube was placed in a freezer at −40° C. and stored frozen until the samples were evaluated. As a control, an aqueous solution of the fish collagen in which the pH was not adjusted was used. Immediately after the addition of transglutaminase to the aqueous solution of the fish collagen, restructured pork was prepared by the same methods.

The restructured frozen pork was sliced into a 9-mm thickness and a 2.5-cm width; after thawing, the binding strength was measured with a texture analyzer manufactured by Stable Micro Systems, Co. The results are shown in Table 4.

TABLE 4 pH dependency of binding strength with transglutaminase and fish collagen

| pH of mixtures of fish collagen and transglutaminase | Adhesion strength (g/cm$^2$) |
|---|---|
| 2.5 | 19 |
| 3 | 150 |
| 4 | 157 |
| 6 | - (gelled) |
| 7 | - (gelled) |
| 8 | - (gelled) |
| 9 | - (gelled) |
| 10 | 169 |
| 11 | 115 |
| 12 | 105 |
| 12.5 | 0 |
| Control (pH 5) | 89 |

When the pH of the aqueous collagen solution was not adjusted, the mixture was gelled via the transglutaminase reaction before the mixture was added to the pork pieces. Accordingly, the mixture could not be used for the production of any restructured food.

When the pH of the aqueous collagen solution was adjusted to a range of pH 3 to pH 4 or a range of pH 10 to 12, the resulting mixture could retain the physical properties suitable for mixing with the pork pieces for a time period sufficient for mixing procedures and also could attain sufficient binding strength in the final product.

Further, the pH after mixing with the pork pieces was measured. The pH of the meat surface in any of the experimental lots was shifted to pH 5 to pH 7. In all the experimental lots with the mixed meat pieces, the pH was shifted to the pH range where the transglutaminase reaction is expressed through the mixing with the meat pieces. In the experimental lots with the aqueous collagen solutions at pH 2.5 and pH 12.5, transglutaminase was inactivated before the mixing with the meat pieces, so that the binding strength via the transglutaminase reaction was poor or non-existent.

EXAMPLE 4

Production of Restructured Beef with Transglutaminase and Fish Collagen (Powder Sprinkling Methods)

As shown in Table 5 below, six types of enzyme preparations were prepared. The enzyme preparations were deposited on the surface of beef thigh meat pieces (about 2-cm cube); two of such meat pieces closely adhered together on the surfaces with one of the enzyme preparations deposited, followed by vacuum sealing. The amount of transglutaminase then used was 0.64 U per one gram of the final product, while the fish collagen was used at an amount of 0.003 g per one gram of the final product.

The control is an enzyme preparation in which the blend of sodium carbonate (enzyme preparation 1 in Table 5 below) was not used.

Herein, the fish collagen used in Example 1 and the transglutaminase used in Example 1 ("Activa" TG at a specific activity of 1,000 U/g product manufactured by Ajinomoto Co., Inc.) were used as the collagen and the transglutaminase, respectively.

After maintaining the resulting beef pieces at 5° C. for 2 hours to effectuate the transglutaminase reaction, the binding strength of the two meat pieces was measured with a texture analyzer manufactured by Stable Micro Systems, Co., Ltd. at a tensile test (Table 6). Herein, Table 6 shows the pHs of the meat surfaces with these enzyme preparations along with the pHs of the aqueous 20% solutions of the individual enzyme preparations.

TABLE 5

Compositions of enzyme preparations

| Materials | Composition ratio (% by weight) | | | | | |
|---|---|---|---|---|---|---|
| | 1. (control) | 2. | 3. | 4. | 5. | 6. |
| Transglutaminase | 6 | 6 | 6 | 6 | 6 | 6 |
| Fish collagen | 30 | 30 | 30 | 30 | 30 | 30 |
| Lactose | 64 | 63 | 62 | 61 | 59 | 54 |
| Sodium carbonate | 0 | 1 | 2 | 3 | 5 | 10 |
| Total | 100 | | | | | |

TABLE 6

Relation of the binding strength of restructured beef using various enzyme preparations with the pHs (of the aqueous enzyme preparation solutions and the restructured meat surfaces)

| | 1. (control) | 2. | 3. | 4. | 5. | 6. |
|---|---|---|---|---|---|---|
| Binding strength (g/cm$^2$) | 241 | 280 | 320 | 428 | 395 | 329 |
| pH of aqueous 20% enzyme preparation solution | 5.3 | 9.5 | 9.9 | 10.2 | 10.5 | 10.8 |
| pH of meat surface with enzyme preparation deposited | 5.5 | 5.9 | 6.2 | 6.7 | 7.1 | 7.8 |

The enzyme preparations in the experimental lots 2 to 6, when dissolved in water, were at pH 9 or more to pH 12 or less. When deposited on the meat pieces, the surfaces of the meat pieces shifted to a range of pH 5 or more to pH 8 or less, namely the pH range where the transglutaminase reaction was carried out via the pH buffer effects thereof. Because the binding strength levels in any of the experimental lots were higher than that in the control lot 1, the enzyme preparations containing the alkaline substance enhanced the binding strength more greatly than the enzyme preparation with no content of the alkaline substance did.

As evidenced by the foregoing, immediate gelation of a solution of transglutaminase and collagen in a mixture can be suppressed and, thus processability of the production of food products (e.g., restructured food) can be improved. Additionally, by using the enzyme preparation of the present invention, food materials can adhere together strongly. Thus, in one embodiment, the enzyme preparation of the present invention can be used for both (i) a method of dissolving the enzyme preparation in water or (ii) a fluid material to prepare a paste-like material for use as a binder (water solution methods) and the method of directly sprinkling the enzyme preparation on a solid food material for binding (powder sprinkling methods). Therefore, such enzyme preparation is very useful as an enzyme preparation with wide applicability.

Numerous modifications and variations on the present invention are possible in light of the above teachings. It is, therefore, to be understood that within the scope of the accompanying claims, the invention may be practiced otherwise than as specifically described herein.

The invention claimed is:

1. A method for producing a food product, comprising
dissolving the enzyme preparation in a solution,
shifting the pH of the resulting solution to a pH range where the expression of transglutaminase activity is suppressed, and
mixing the solution and a food material to shift the pH of the resulting mixture back to a pH range where the transglutaminase activity is expressed whereupon a transglutaminase reaction is carried out,
wherein said enzyme preparation comprises:
a transglutaminase;
collagen; and
an acidic or alkaline substance shifting the pH of the enzyme preparation, when dissolved in a solution, to a pH range wherein the expression of transglutaminase activity is suppressed,
wherein the pH range where the expression of transglutaminase is suppressed is pH 3 or more to less than pH 5 or pH 10-12.

2. The method of claim 1, wherein the pH range where the expression of transglutaminase activity is suppressed when the enzyme preparation is dissolved in the solution is pH 3 or more to less than pH 5.

3. The method of claim 1, wherein the pH range where the expression of transglutaminase activity is suppressed when the enzyme preparation is dissolved in the solution is pH 10-12.

4. The method of claim 1, wherein the acidic or alkaline substance is one or more selected from the group consisting of citric acid, malic acid, tartaric acid, sodium carbonate, potassium carbonate, trisodium phosphate, tripotassium phosphate, tetrasodium pyrophosphate, tetrapotassium pyrophosphate, glycine sodium salt, glycine potassium salt, sodium hydroxide, potassium hydroxide and calcium oxide.

5. The method of claim 1, wherein the collagen is derived from fish or shellfish.

6. The method of claim 1, wherein said solution is water.

7. The method of claim 1, wherein said enzyme preparation comprises:
a transglutaminase;
collagen; and an alkaline substance shifting the pH of the enzyme preparation, when dissolved in a solution, to a range of pH 9-12 and being directly mixed with a food material.

8. The method of claim 7, wherein the alkaline substance is one or more selected from the group consisting of sodium carbonate, potassium carbonate, trisodium phosphate, tripotassium phosphate, tetrasodium pyrophosphate, tetrapotassium pyrophosphate, glycine sodium salt, glycine potassium salt, sodium hydroxide, potassium hydroxide and calcium hydroxide and calcium oxide.

9. The method of claim 7, wherein the collagen is derived from fish or shellfish.

10. The method for producing a food product according to claim 1, wherein the pH range where the transglutaminase activity is expressed is pH 5-8.

11. The method for producing a food product according to claim 1, wherein the food product is a gel-like food or a restructured food wherein said gel-like food is selected from the group consisting of a jelly containing vegetable pieces, a jelly containing fruit pieces, a jelly bean, a gummy candy, and a shark fin food product.

12. A method for producing a food product, comprising
directly mixing the enzyme preparation to food materials to conduct the transglutaminase reaction,
wherein said enzyme preparation comprises:
a transglutaminase;
collagen; and
an acidic or alkaline substance shifting the pH of the enzyme preparation, when dissolved in a solution, to a pH range wherein the expression of transglutaminase activity is suppressed.

13. The method for producing a food product according to claim 12, wherein the food product is a restructured product.

14. A method for producing a food product, comprising
directly mixing the enzyme preparation to food materials to conduct the transglutaminase reaction,
wherein said enzyme preparation comprises:
a transglutaminase;
collagen derived from fish or shellfish; and
an acidic or alkaline substance shifting the pH of the enzyme preparation, when dissolved in a solution, to a pH range wherein the expression of transglutaminase activity is suppressed.

15. The method for producing a food product according to claim 14, wherein the food product is a restructured product.

16. A method for producing a food product, comprising
dissolving the enzyme preparation in a solution,
shifting the pH of the resulting solution to a pH range where the expression of transglutaminase activity is suppressed, and
injecting the resulting solution into a food material whereupon a transglutaminase reaction is carried out,
wherein said enzyme preparation comprises:
a transglutaminase;
collagen; and
an acidic or alkaline substance shifting the pH of the enzyme preparation, when dissolved in a solution, to a pH range wherein the expression of transglutaminase activity is suppressed.

17. The method for producing a food product according to claim 16, wherein the pH range where the expression of transglutaminase activity is suppressed is pH 3 or more to less than pH 5 or pH 10-12.

18. The method for producing a food product according to claim 16, wherein the food product is a whole muscle product produced without using minced meat.

19. A method for producing a food product, comprising
dissolving in a solution (1) transglutaminase, (2) collagen, and (3) an acidic or alkaline substance shifting the pH of the resulting solution to a pH range where the expression of transglutaminase activity is suppressed and
mixing food materials with the resulting solution to shift the pH of the resulting mixture back to a pH range where the transglutaminase activity is expressed whereupon a transglutaminase reaction is carried out.

\* \* \* \* \*